United States Patent
Staller

(10) Patent No.: US 6,555,856 B1
(45) Date of Patent: Apr. 29, 2003

(54) SEMICONDUCTOR DEVICE WITH MEANS FOR VERIFYING A HERMETIC SEAL THEREFOR

(75) Inventor: Steven Edward Staller, Russiaville, IN (US)

(73) Assignee: Delphi Technologies, Inc., Troy, MI (US)

(*) Notice: Subject to any disclaimer, the term of this patent is extended or adjusted under 35 U.S.C. 154(b) by 0 days.

(21) Appl. No.: 09/534,587

(22) Filed: Mar. 27, 2000

Related U.S. Application Data

(62) Division of application No. 09/098,291, filed on Jun. 16, 1998, now Pat. No. 6,074,891.

(51) Int. Cl.$^7$ ................................. H01L 27/14
(52) U.S. Cl. ................. 257/252; 257/253; 257/254
(58) Field of Search .................. 257/252, 253, 257/254; 438/50, 51, 52, 53

(56) References Cited

U.S. PATENT DOCUMENTS 4,054,875 A * 10/1977 Cachier ................. 331/107 DP
5,837,562 A * 11/1998 Cho ........................ 438/118
6,049,313 A * 4/2000 Sawada et al. ........... 343/776
6,282,352 B1 * 8/2001 Kato et al. ................ 264/1.25

* cited by examiner

Primary Examiner—Kevin M. Picardat
(74) Attorney, Agent, or Firm—JImmy L. Funke

(57) ABSTRACT

A method and device for verifying whether a cavity (16) enclosing a micromachined sensing structure (14) between a pair of wafers (10, 12) is hermetically sealed by detecting the presence of moisture within the cavity (16). The method entails forming a bare, unpassivated PN junction diode (20) in a semiconductor substrate, preferably a device wafer (10) with the sensing structure (14). The device wafer (10) is then bonded to a capping wafer (12) to enclose the PN junction diode (20) and micromachine (14) within a cavity (16) defined by and between the wafers (10, 12). The reverse diode characteristics of the PN junction diode (20) are then determined by causing a reverse current to flow through the diode (20). For this purpose, either a known voltage is applied across the diode (20) and the reverse leakage current measured, or a known reverse current is forced across the diode (20) and the voltage measured. The unpassivated junction diode (20) exhibits unstable current/voltage readings if sufficient moisture is present within the cavity (16), thereby indicating whether or not the cavity (16) is hermetically sealed.

9 Claims, 1 Drawing Sheet

SEMICONDUCTOR DEVICE WITH MEANS FOR VERIFYING A HERMETIC SEAL THEREFOR

CROSS REFERENCE TO RELATED APPLICATIONS

This is a divisional patent application of U.S. patent application Ser. No. 09/098,291, filed Jun. 16, 1998, now U.S. Pat. No. 6,074,891.

FIELD OF THE INVENTION

The present invention generally relates to methods for verifying whether a cavity is hermetically sealed, such as when semiconductor wafers are bonded together to hermetically enclose a micromachined sensing structure. More particularly, this invention relates to an electrical verification technique and device for detecting moisture within a cavity enclosing a micromachine sensing structure as an indication of whether the sensing structure is hermetically sealed within the cavity.

BACKGROUND OF THE INVENTION

Within the semiconductor industry, there are numerous applications that require bonding a semiconductor wafer to a second wafer or glass, an example being sensors formed by a silicon wafer (referred to herein as a device wafer) with a micromachined sensing structure (micromachine), which is capped by a semiconductor or glass wafer (referred to herein as a capping wafer). Examples of semiconductor sensors include yaw (angular rate) sensors, accelerometers and pressure sensors, each of which typically entails a cavity that encloses the micromachine between the wafers. Absolute pressure sensors require that the cavity be evacuated and hermetically sealed, while the performance of yaw sensors with resonating micromachines generally benefit if the cavity is evacuated so that the micromachine operates in a vacuum.

By the very nature of their operation, micromachines must be free to move to some degree, necessitating that the seal between the wafers is sufficient to exclude foreign matter from the cavity. A hermetical seal ensures that moisture is also excluded, which would form ice crystals at low temperatures that could impede motion of the micromachine. Accordingly, the integrity of the bond between the wafers is essential to the life of a semiconductor sensor. Various bonding techniques have been used for the purpose of maximizing the strength and reliability of the bond. For example, the use of adhesives, dielectrics such as glass frit, and solders as intermediate bonding materials has been suggested in the prior art. Silicon direct and anodic bonding techniques that do not require an intermediate material have also been used. As would be expected, the conditions vary under which each of these bonding techniques will reliably yield a hermetic seal.

While each of these sealing methods has found wide use, sensors are inevitably produced whose cavities are not hermetically sealed after the bonding operation. To reduce returns and field failures, devices with inadequate seals need to be identified following the bonding operation. Labor intensive visual inspections can be useful to screen out unsealed devices, but are expensive and compromised by the likelihood of human error. Various automated inspection techniques are also available, though each have limitations and are often expensive to implement in a large-scale assembly process.

SUMMARY OF THE INVENTION

It is an object of this invention to provide a method for determining whether a hermetically sealed cavity has been achieved between a semiconductor wafer and a capping wafer.

It is another object of this invention that such a method employs a PN junction diode to sense the presence of moisture within the cavity as an indication of whether the seal is hermetic or not.

It is yet another object of this invention that such a method can be readily performed in a large-scale assembly process.

It is still another object of this invention that such a method is useful to inspect semiconductor sensors with micromachine sensing structures.

In accordance with a preferred embodiment of this invention, these and other objects and advantages are accomplished as follows.

According to the present invention, there is provided a method and device for verifying whether a cavity enclosing a micromachined sensing structure between a pair of wafers is hermetically sealed. The invention entails an electrical verification technique and semiconductor device that detects moisture within the cavity as an indication of whether the sensing structure is hermetically sealed within the cavity.

The method of this invention generally entails forming a bare, unpassivated PN junction diode in a semiconductor substrate, preferably a device wafer having a micromachine sensing structure. For example, the PN junction diode can be formed by implanting a P-type region in an N-type epitaxial layer of the device wafer. The device wafer is then bonded to a capping wafer of any suitable material to enclose the PN junction diode and micromachine within a cavity defined by and between the wafers. Bonding can be achieved by a variety of methods, including silicon direct bonding, silicon fusion bonding, anodic bonding and glass frit. The reverse diode characteristics of the PN junction diode are then determined by causing a reverse current to flow through the diode. For this purpose, either a known voltage is applied across the diode and the reverse leakage current measured, or a known reverse current is forced through the diode and the voltage measured. According to the invention, while passivated PN junction diodes are essentially unaffected by moisture, the unpassivated junction diode of this invention will exhibit unstable current/voltage readings if sufficient moisture is present within the cavity, which indicates whether or not the cavity is hermetically sealed.

Using the method of this invention, processing of a semiconductor sensor is only slightly altered to include the unpassivated PN diode junction within the cavity, and testing after wafer bonding is a matter of measuring the voltage or current through the diode. Accordingly, the present invention provides a low-cost inspection method that is not labor intensive and can be readily implemented in a large-scale assembly process, yet is highly reliable at detecting sensors having cavities that are not hermetically in order to reduce returns and field failures.

Other objects and advantages of this invention will be better appreciated from the following detailed description.

BRIEF DESCRIPTION OF THE DRAWINGS

The present invention will now be described, by way of example, with reference to the accompanying drawings, in which.

DETAILED DESCRIPTION OF THE INVENTION

Figure 1:
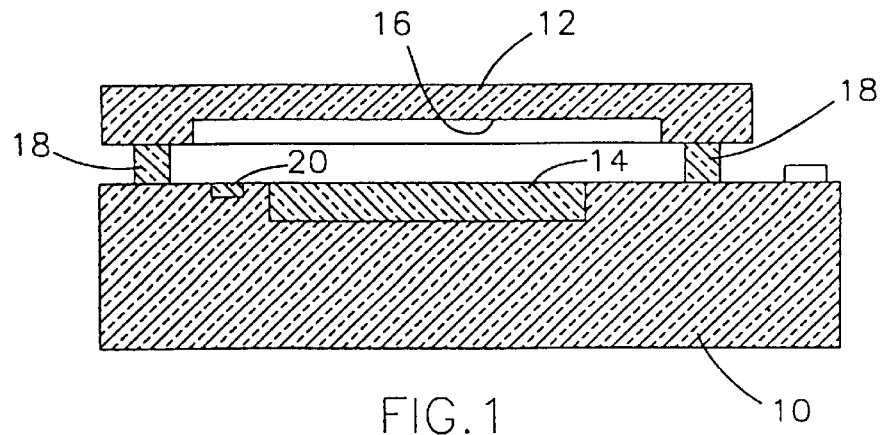
FIG. 1 is a cross-sectional view of a semiconductor sensor assembly that includes a device wafer, capping wafer and micromachine sensing structure, and further includes an unpassivated PN junction diode for determining whether a hermetic seal exists between the wafers in accordance with this invention.
Figure 2:
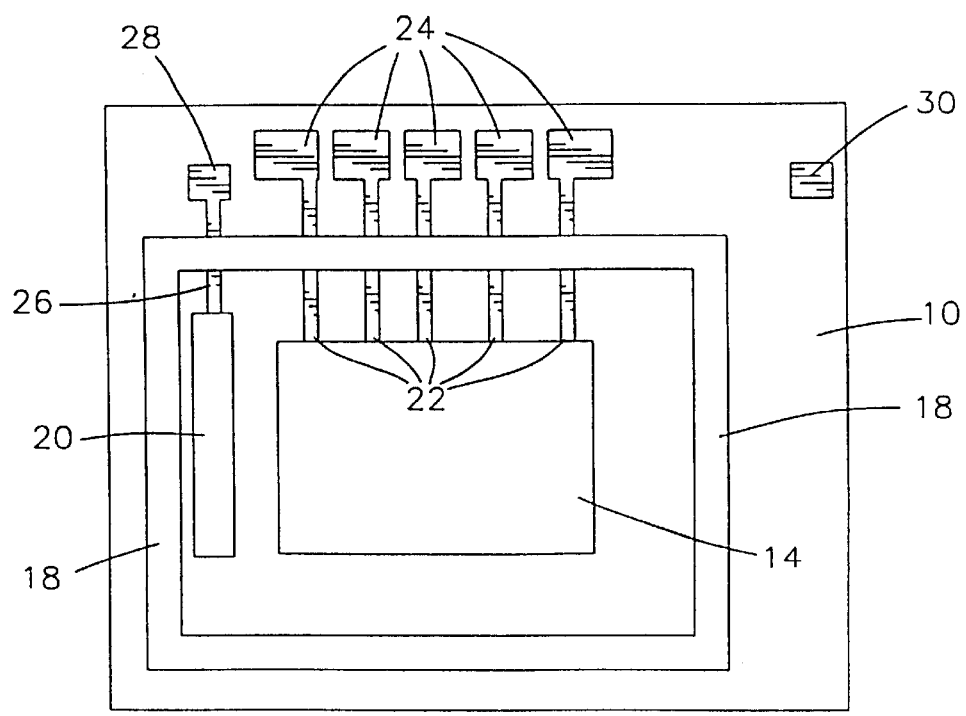
FIG. 2 is a plan view of the device wafer of FIG. 1.
Figure 3:
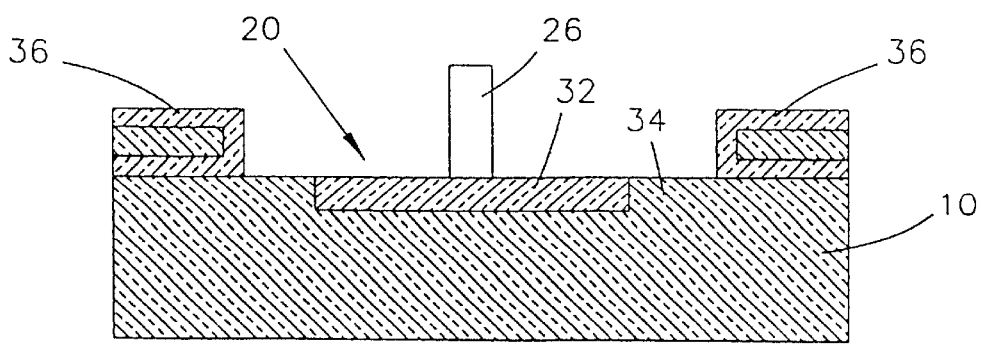
FIG. 3 is a cross-sectional view showing the PN junction diode of FIGS. 1 and 2 in greater detail.

FIGS. 1 through 3 represent a semiconductor sensor in accordance with this invention. The sensor is formed by bonding a device wafer 10 to a capping wafer 12, such that a micromachine 14 is enclosed within a hermetically-sealed cavity 16 between the wafers 10 and 12. The wafers 10 and 12 are preferably silicon, and the device wafer 10 preferably monocrystallographic silicon, though it is foreseeable that other materials could be used. For example, the capping wafer 12 can be formed of glass, ceramic, or another semiconducting material. The micromachine 14 can be of any suitable type, including resonating structures, diaphragms and cantilevers that rely on capacitive, piezoresistive and piezoelectric sensing elements to sense motion, pressure, etc., all of which are known in the art.

As is conventional, the micromachine 14 is electrically interconnected to metal bond pads 24 on the device wafer 10 by conductive runners 22. As shown in FIG. 2, the runners 22 cross beneath a bond material 18, such as a glass frit, between the mating surfaces of the device and capping wafers 10 and 12. However, the invention does not require the use of an intermediate bond material, but can also employ silicon direct bonding (SDB) methods, including silicon fusion bonding (SFB), by which the device and capping wafers 10 and 12 are bonded without intermediate bond, alloy and adhesive films. With the bond pads 24, the micromachine 14 and its associated sensing elements are electrically interconnected with appropriate signal conditioning circuitry that may be formed on the device wafer 10, the capping wafer 12 or a separate chip.

According to the invention, the micromachine 14 is hermetically sealed, optionally in a vacuum, within the cavity 16, and the integrity of the seal is verified by the presence of a bare PN junction diode 20 present within the cavity 16, preferably in close proximity to the micromachine 14 as indicated in FIG. 2. As understood by those skilled in the art, the diode 20 requires contiguous P-type and N-type regions, such as the P-type implant 32 formed in an N-type epitaxial layer 34 on the device wafer 10 as shown in FIG. 3. Contrary to conventional PN junction diodes used in microelectronics that require passivation (e.g., one or more thermal oxide or nitride layers) or another protective coating to exhibit stable PN junction characteristics, the PN junction diode 20 of this invention is bare, used herein to denote that passivation and other protective films are not present over the diode 20. As portrayed in FIG. 3, passivation layers 36 that protect the surface of the device wafer 10 within the cavity 16 do not cover or protect the diode 20.

According to this invention, without such protection, the junction characteristics of the diode 20 are notably degraded by the presence of moisture in the cavity 16. More particularly, the bare PN junction diode 20 of this invention has a relatively low reverse breakdown voltage when exposed to certain levels of humidity, which is excluded from the cavity 16 during the wafer bonding process and can only be reintroduced by the ingress of moisture-laden air through a flaw in the bond between the wafers 10 and 12. As a result, excessive levels of humidity within the cavity 16, generally on the order of about 40% relative humidity (RH) or more, can be detected by forcing a sufficiently high reverse current through the diode 20 and measuring the resulting voltage, or by applying a known voltage to the diode 20 and measuring the reverse current. For this purpose, a metal runner 26 is provided to interconnect the P-type region of the diode 20 (e.g., the P-type implant 32) with a metal bond pad 28 on the device wafer 10 outside the cavity 16. Connection to the N-type region of the diode 20 (e.g., the N-type epitaxial layer 34) is made with a second metal bond pad 30.

The bare PN junction diode 20 of this invention can be formed by several processes. Generally, the area and doping profiles can be chosen on the basis of the packaging constraints for the device in which the diode 20 is to be used. The diode 20 can be formed as part of the normal process flow for the device, by which the diode 20 is never passivated. However, exposing the bare diode 20 to certain processes, such as metal sputtering, can have a negative impact on diode quality. An alternative is to passivate the diode 20 along with the other regions of the device wafer 10, and then add a mask and etch step to remove the passivation after the mask/etch step is performed for the bond pads 24, 28 and 30. However, the extra mask/etch step is undesirable, particularly after the micromachine 14 has been formed. A preferred approach is to remove the passivation from the diode 20 during the bond pad mask/etch step. This process requires an extended pad etch beyond that typically required and used for the metal bond pads 24. While not adversely affecting the bond pads 24, this approach may require resizing some mask levels to account for the extra undercut of both plasma oxide and thermal oxide on the device wafer 10. In practice, no adverse effects (e.g., repassivation of the diode 20 by thermal oxidation) have been observed as a result of the PN junction diode being exposed during subsequent etching and bonding operations, including the process of silicon direct bonding the device and capping wafers 10 and 12.

During an investigation leading to this invention, bare PN junction diodes were evaluated in comparison to passivated PN junction diodes having essentially identical doping profiles and areas. Given the geometry and doping profiles of the diodes, it was determined that the breakdown voltage of the passivated diodes was about fifty volts, and that the reverse leakage current at about seventeen volts would be expected to be less than about 500 n amps. In a relative humidity of about 80% RH, and with an applied voltage of about seventeen volts across each of the diodes, current readings were taken over a period of 0.2 to 17 seconds, with the results summarized in Table I below.

TABLE I

| Time | Leakage (Reverse) Current ($\mu$A) | |
| --- | --- | --- |
| (Seconds) | Passivated Diode | Bare Diode |
| 0.2 | 0.129 | 0.160 |
| 3.0 | 0.073 | 0.871 |
| 3.5 | 0.043 | 0.868 |
| 4.0 | 0.047 | 1.287 |
| 5.0 | 0.055 | 2.012 |
| 7.0 | 0.047 | 4.246 |
| 9.0 | 0.040 | 6.713 |
| 11.0 | 0.036 | 8.442 |
| 13.0 | 0.030 | 10.113 |
| 15.0 | 0.028 | 11.495 |
| 17.0 | 0.028 | 12.200 |

The above results evidence that the passivated diode remained stable (nearly ideal) at the tested voltage, but that the bare diode of this invention initially exhibited low reverse current (comparable to the passivated diode) but became unstable within seconds, illustrating the transient nature of the unpassivated (non-ideal) diode. Notably, the reverse current had increased for the bare diode by a factor of ten after four seconds, suggesting that a delay time of four seconds can be adequate to identify inadequate seals.

During a second investigation, bare and passivated PN junction diodes essentially identical to those tested above were evaluated by forcing one µamp of reverse current through the diodes and then measuring the corresponding voltage following delay times of 0.2 and 3 seconds. The results are summarized in Table II below.

TABLE II

| Time | Voltage at 1 µamp Reverse Current | |
|---|---|---|
| (Seconds) | Passivated Diode | Bare Diode |
| 0.2 | 51.0 | 51.0 |
| 3.0 | 52.6 | 12.8 |

These results evidenced that the passivated diode yielded stable readings for time delays of 0.2 and 3 seconds, but that the reading for the bare diode of this invention decreased by a factor of four after only 3 seconds. On this basis, it was concluded that the technique of forcing current and measuring voltage was preferred because the delay time required to get statistically significant reading changes was shorter with forced current (Table II) than with applied voltage (Table I).

On the basis of the above, further testing was conducted with bare and passivated diodes essentially identical to those tested above, but in a hermetically sealed environment containing less than 10% RH. As done for the specimens reported in Table I, a voltage of about seventeen volts was applied across each of the diodes, with the reverse leakage current read and recorded. The results are summarized in Table III below, and evidence that the stability of a bare PN junction diode is comparable to that of a passivated PN junction diode when moisture is substantially absent. The decrease in current over time was attributable to wafer level issues and not the diode structures tested.

TABLE III

| Time | Leakage (Reverse) Current (µA) | |
|---|---|---|
| (Seconds) | Passivated Diode | Bare Diode |
| 0.2 | 0.058 | 0.066 |
| 3.0 | 0.033 | 0.034 |
| 5.0 | 0.031 | 0.028 |
| 7.0 | 0.030 | 0.026 |
| 9.0 | 0.030 | 0.026 |
| 11.0 | 0.030 | 0.026 |
| 13.0 | 0.028 | 0.034 |
| 15.0 | 0.028 | 0.030 |
| 17.0 | 0.030 | 0.038 |

From the above, it was concluded that the bare PN junction diodes evaluated were insensitive to relative humidities of less than 10%, but would detect leaks in a bonded wafer assembly exposed to humidity levels typically seen during processing, e.g., that used to generate the data of Tables I and II, and generally relative humidities of 85% and higher. Further testing has indicated that the unpassivated PN junction diodes 20 of this invention are affected by moisture at humidity levels as low as about 40% RH, though it is foreseeable that the sensitivity of a bare PN junction diode may be greater or less under different conditions.

While the invention has been described in terms of a preferred embodiment, it is apparent that other forms could be adopted by one skilled in the art. Accordingly, the scope of the invention is to be limited only by the following claims.

What is claimed is:

1. A semiconductor sensor comprising:

a semiconductor wafer bonded to a capping wafer so as to define a cavity therebetween;

an unpassivated PN junction diode in a first surface region of the semiconductor wafer and enclosed within the cavity;

a micromachine sensing structure in a second surface region of the semiconductor wafer and enclosed within the cavity; and a reverse current flowing through the unpassivated PN junction diode, wherein a reverse current or voltage caused by the reverse current is an indication of the presence of moisture within the cavity.

2. A semiconductor sensor comprising:

a device wafer bonded to a capping wafer so as to define a cavity therebetween;

a bare PN junction diode in a semiconductor substrate enclosed within the cavity; and means for flowing a reverse current through the bare PN junction diode, wherein the reverse current or voltage caused by the reverse current is an indication of the presence of moisture within the cavity.

3. A semiconductor sensor according to claim 2, further comprising a reverse current flowing through the bare PN junction diode.

4. A semiconductor sensor comprising:

a device wafer bonded to a capping wafer so as to define a cavity therebetween; and a bare PN junction diode in a semiconductor substrate enclosed within the cavity.

5. A semiconductor sensor according to claim 4, further comprising a micromachine on the device wafer.

6. A semiconductor sensor according to claim 4, wherein the semiconductor substrate is N-type and the bare PN junction diode comprises a P-type region in the N-type semiconductor substrate.

7. A semiconductor sensor according to claim 4, further comprising a reverse current flowing through the bare PN junction diode, wherein a reverse current or voltage caused by the reverse current is an indication of the presence of moisture within the cavity.

8. A semiconductor sensor according to claim 4, wherein the bare PN junction diode is unpassivated.

9. A semiconductor sensor according to claim 4, wherein the device wafer is bonded to the capping wafer with a bond chosen from the group consisting of a silicon direct bond, an anodic bond and a glass frit bond.

* * * * *